(12) United States Patent
Kiani et al.

(10) Patent No.: US 8,740,792 B1
(45) Date of Patent: Jun. 3, 2014

(54) PATIENT MONITOR CAPABLE OF ACCOUNTING FOR ENVIRONMENTAL CONDITIONS

(75) Inventors: Massi Joe E. Kiani, Laguna Niguel, CA (US); Marcelo Lamego, Coto De Caza, CA (US); Michael O'Reilly, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 149 days.

(21) Appl. No.: 13/179,017

(22) Filed: Jul. 8, 2011

Related U.S. Application Data

(60) Provisional application No. 61/363,320, filed on Jul. 12, 2010.

(51) Int. Cl.
*A61B 5/00* (2006.01)
(52) U.S. Cl.
USPC .......................................... 600/301; 600/323
(58) Field of Classification Search
None
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |

(Continued)

OTHER PUBLICATIONS

U.S. Appl. No. 61/363,320, filed Jul. 2010, Kiani et al.

*Primary Examiner* — Gary Jackson
*Assistant Examiner* — Shirley Jian
(74) *Attorney, Agent, or Firm* — Knobbe, Martens, Olson and Bear, LLP

(57) ABSTRACT

A patient monitoring system includes a sensor, a patient monitor and an environmental conditions module. The patient monitor receives signals indicative of measurements of physiological parameters from the sensor, as well as data indicative of one or more environmental conditions from the environmental conditions module. The patient monitor determines one or more measurements of one or more physiological parameters based on the signals received from the sensor and the data indicative of one or more environmental conditions.

20 Claims, 3 Drawing Sheets

(56) References Cited

U.S. PATENT DOCUMENTS

| | | | |
|---|---|---|---|
| 5,645,440 | A | 7/1997 | Tobler et al. |
| 5,685,299 | A | 11/1997 | Diab et al. |
| 393,830 | A | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |

(56) References Cited

U.S. PATENT DOCUMENTS

| | | |
|---|---|---|
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,468,040 B2 * | 12/2008 | Hartley et al. ................ 600/529 |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,572,225 B2 * | 8/2009 | Stahmann et al. ............ 600/484 |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 7,993,279 B2 * | 8/2011 | Hartley et al. ................ 600/529 |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 * | 10/2011 | Diab et al. .................... 600/323 |
| 8,046,042 B2 | 10/2011 | Diab et al. |
| 8,048,040 B2 | 11/2011 | Kiani |
| 8,050,728 B2 | 11/2011 | Al-Ali et al. |
| 8,346,332 B2 * | 1/2013 | Kuhn et al. .................... 600/323 |
| 8,463,346 B2 * | 6/2013 | Kuhn et al. .................... 600/323 |
| 2005/0080348 A1 * | 4/2005 | Stahmann et al. ............ 600/529 |
| 2005/0085738 A1 * | 4/2005 | Stahmann et al. ............ 600/529 |
| 2008/0312548 A1 * | 12/2008 | Hartley et al. ................ 600/534 |

* cited by examiner

PATIENT MONITOR CAPABLE OF ACCOUNTING FOR ENVIRONMENTAL CONDITIONS

PRIORITY CLAIM TO RELATED PROVISIONAL APPLICATION

The present application claims the benefit under 35 U.S.C. §119(e) to U.S. Provisional Application No. 61/363,320, filed Jul. 12, 2010, entitled PATIENT MONITOR CAPABLE OF ACCOUNTING FOR ENVIRONMENTAL CONDITIONS, herein incorporated by reference in its entirety.

BACKGROUND

Pulse oximetry utilizes a noninvasive sensor to measure various physiological parameters, such as oxygen saturation ($SpO_2$) and pulse rate of a person. The sensor has light emitting diodes (LEDs) that transmit optical radiation of various wavelengths into a tissue site and a detector that responds to the intensity of the optical radiation after attenuation by pulsatile arterial blood flowing within the tissue site. Pulse oximeters have gained rapid acceptance in a wide variety of medical applications, including surgical wards, intensive care and neonatal units, general wards, home care, physical training, and virtually all type of monitoring scenarios.

Pulse oximeters capable of reading through motion induced noise are disclosed in at least U.S. Pat. Nos. 6,770,028, 6,658,276, 6,584,336, 6,263,222, 6,157,850, 5,769,785, and 5,632,272, which are assigned to Masimo Corporation ("Masimo") of Irvine, Calif. and are incorporated by reference herein. Low noise pulse oximetry sensors are disclosed in one or more of U.S. Pat. Nos. 7,027,849, 6,985,764, 6,934,570 6,760,607 6,377,829 6,285,896 5,782,757 5,638,818, which are also assigned to Masimo and incorporated by reference herein. Moreover, pulse oximeters capable of reading through motion induced noise and low noise optical sensors including LNOP® disposable, reusable and/or multi-site sensors and Radical®, Rad-5™, Rad-8™, Rad-9™, PPO+™, and Pronto-7™ monitors are also available from Masimo.

Multiple parameter monitors and multiple wavelength sensors are described in U.S. patent application Ser. No. 11/367,033 entitled Noninvasive Multiple Parameter Patient Monitor filed Mar. 1, 2006 and U.S. patent application Ser. No. 11/367,013 entitled Multiple Wavelength Sensor Emitters filed Mar. 1, 2006, incorporated by reference herein. Multiple parameter monitors are capable of measuring various physiological parameters, such as oxygen saturation ($SpO_2$), hemoglobin (Hb), oxyhemoglobin ($HbO_2$), total hemoglobin (SpHb™), carboxyhemoglobin (SpCO®), methemoglobin (SpMet®), total oxygen content (SpOC™), perfusion index (PI), pleth variability index (PVI®), pulse rate (PR), and temperature. Moreover, multiple parameter monitors and multiple wavelength sensors including Rad-57™ and Radical-7™ monitors and Masimo Rainbow® brand adhesive and reusable sensors are available from Masimo. MS-brand processor boards incorporating SHARC® DSPs from Analog Devices, Inc. are also available from Masimo.

It has been discovered that variations in environmental conditions, such as atmospheric pressure, altitude, humidity, temperature, and the like can affect the readings of the physiological parameters by the pulse oximeter and multi-parameter monitors. Thus, varying environmental conditions can cause a pulse oximeter and/or a multi-parameter patient monitor to be less accurate.

SUMMARY

An aspect of the disclosure is to provide a patient monitor capable of accounting for environmental conditions in processing signals indicative of one or more physiological parameters. A patient monitor capable of measuring various physiological parameters, such as $SpO_2$, Hb, $HbO_2$, SpHb™, SpCO®, SpOC™, SpMet®, PI, PVI®, PR, patient temperature, and/or other parameters can also include an environmental conditions module. The environmental conditions module can provide the patient monitor with data indicative of various environmental conditions internal or external to the patient monitor, such as atmospheric pressure, altitude, humidity, temperature and the like. The patient monitor can use the data obtained from the environmental conditions module to process the signals indicative of one or more physiological parameters. By accounting for environmental conditions the patient monitor can improve accuracy, among other things.

DETAILED DESCRIPTION

Figure 1:
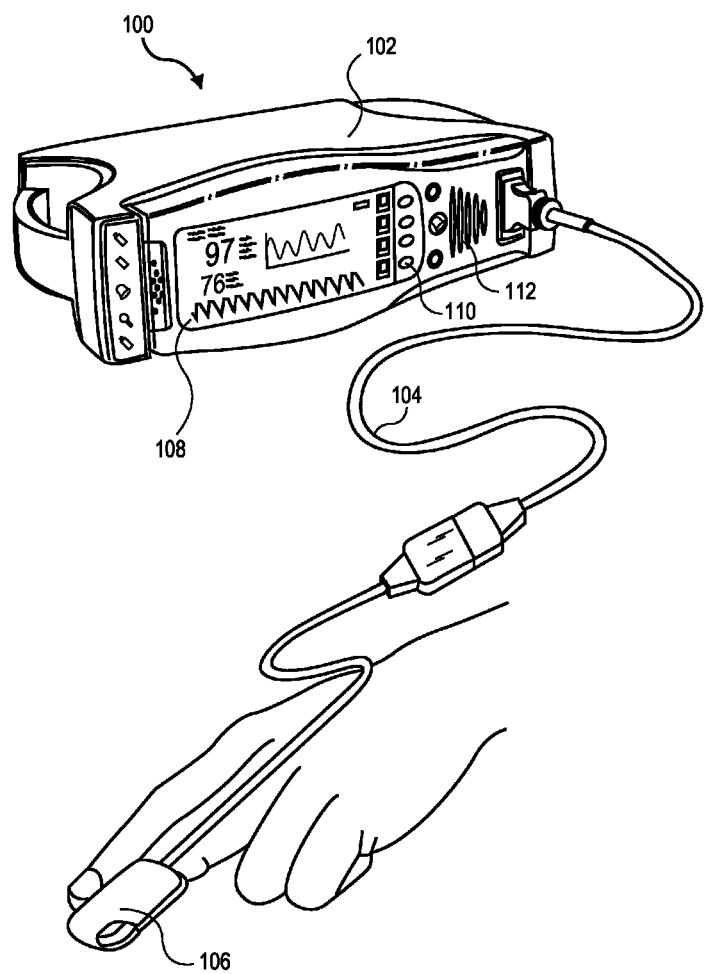
FIG. 1 illustrates an embodiment of a patient monitoring system capable of accounting for environmental conditions in processing signals indicative of physiological parameters.

FIG. 1 illustrates an embodiment of a patient monitoring system 100 configured to determine physiological parameter measurements, such as $SpO_2$, Hb, $HbO_2$, SpHb™, SpCO®, SpOC™, SpMet®, PI, PVI®, PR, temperature, and/or other parameters based on one or more environmental conditions. The patient monitoring system 100 can account for various environmental conditions when calculating the physiological parameter measurements. The patient monitoring system 100 includes a patient monitor 102 in communication with a sensor 106 via a cable 104. The sensor 106 monitors various physiological parameters of a patient and sends signals indicative of the one or more parameters to the patient monitor 102 for processing.

The patient monitor 102 generally includes a display 108, control buttons 110, and a speaker 112 for audible alerts. The display 108 is capable of displaying readings of various monitored patient parameters, which can include numerical readouts, graphical readouts, and the like. The display 108 can also display one or more environmental conditions, such as altitude, temperature, humidity, atmospheric pressure, and the like. Display 108 can be a liquid crystal display (LCD), a cathode ray tube (CRT), a plasma screen, a Light Emitting Diode (LED) screen, Organic Light Emitting Diode (OLED) screen, or any other suitable display. The patient monitor 102 can monitor $SpO_2$, Hb, $HbO_2$, SpHb™, SpCO®, SpOC™, SpMet®, PI, PVI®, PR, temperature, and/or other parameters. An embodiment of a patient monitoring system 100 according to the present disclosure is capable of measuring and displaying trending data of the various parameters, including environmental condition, and preferably is capable of conducting data analysis as to the trending. It is to be understood by one skilled in the art that the patient monitor 102 can come in various, shapes, sizes and configurations without departing from the spirit and scope of the description. For example, the patient monitor 102 can be larger, smaller, portable, comprise varying size displays 108, and the like. In addition, as discussed below in greater detail with reference to FIG. 2, the patient monitor 102 can also include an environmental conditions module, which can provide the patient monitor 102 with information regarding current and/or past environmental conditions. The information from the environmental conditions module can allow the patient monitor 102 to account for various environmental conditions when processing the signals indicative of one or more physiological parameters. As such, the patient monitor 102 can more accurately calculate the physiological parameters of a patient.

As will be discussed in greater detail below with reference to FIG. 2, the sensor 106 can be one of many different types. For example, the sensor 106 can be disposable, reusable, multi-site, partially reusable, partially disposable, be adhesive or non-adhesive, monitor the physiological parameters using reflectance, transmittance, or transreflectance, and can be placed on a finger, hand, foot, forehead, or ear, and can be a stereo sensor or a two-headed sensor. Thus, one of skill in the art will appreciate that sensor 106 can be any number of different types of sensors without departing from the spirit and scope of the disclosure.

Figure 2:
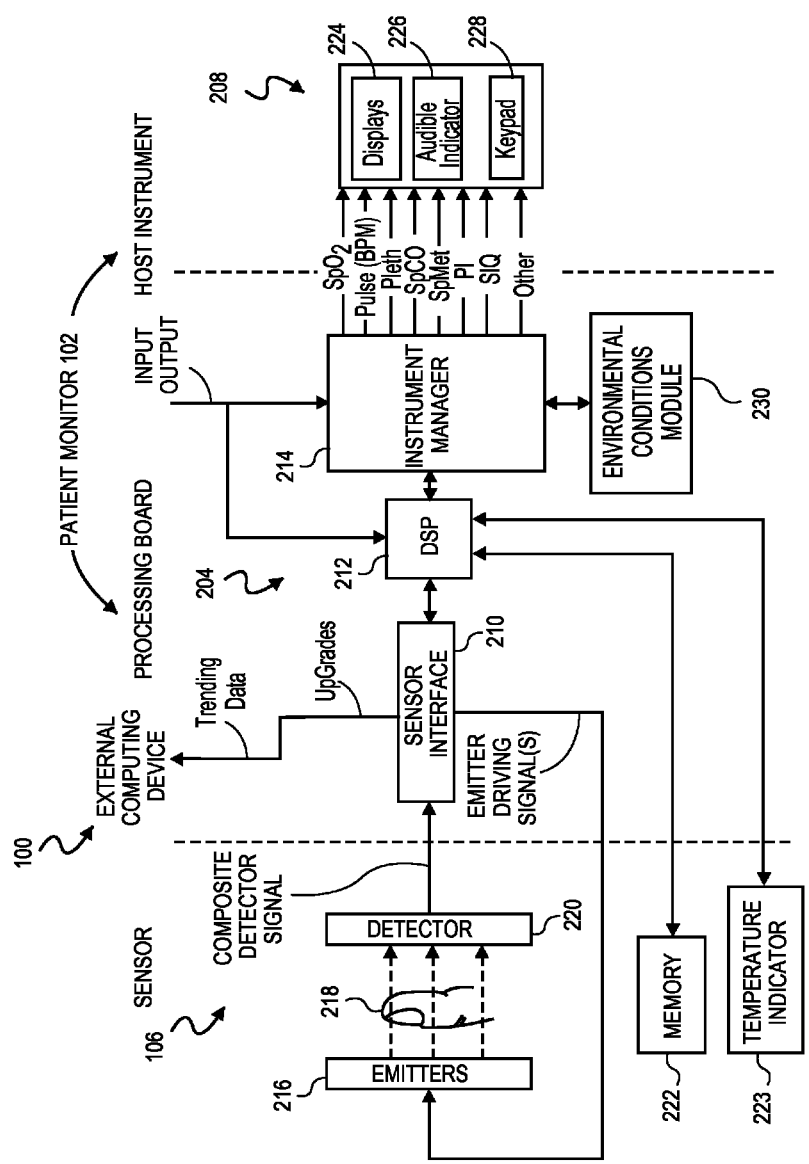
FIG. 2 is a block diagram illustrating an embodiment of a patient monitoring system.

FIG. 2 is a block diagram illustrative of an embodiment of a patient monitoring system 100. As shown in FIG. 2, the patient monitoring system 100 can include a sensor 106 in communication with a patient monitor 102. The sensor 106 can communicate with the patient monitor 102 via wired or wireless communication. The patient monitor 102 can include a processing board 204 and a host instrument 208.

As shown in FIG. 2, the sensor 106 includes a plurality of emitters 216 irradiating the body tissue 218 with differing wavelengths of light, and one or more detectors 220 capable of detecting the light after attenuation by the tissue 218 and transmitting representative signals to the patient monitor 102. In an embodiment, the emitters 216 comprise a matrix of eight (8) emission devices mounted on a flexible substrate, the emission devices being capable of emitting eight (8) differing wavelengths of light. In other embodiments, the emitters 216 can comprise twelve (12) or sixteen (16) emitters, although other numbers of emitters are contemplated, including two (2) or more emitters. As shown in FIG. 2, the sensor 106 can include other electrical components such as, for example, a memory device 222 comprising an EPROM, EEPROM, ROM, RAM, microcontroller, combinations of the same, and the like. In an embodiment, other sensor components can include a temperature determination device 223 or other mechanisms for, for example, determining real-time emission wavelengths of the emitters 216.

The memory 222 can advantageously store some or all of a wide variety of data and information, including, for example, information on the type or operation of the sensor 106; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., SpHb, SpCO, SpMet, Hb, $HbO_2$ and the like), calibration or parameter coefficient data, software such as scripts, executable code, and the like, sensor electronic elements, whether the sensor 106 is a disposable, reusable, multi-site, partially reusable, partially disposable sensor, whether it is an adhesive or non-adhesive sensor, whether the sensor 106 is a reflectance, transmittance, or transreflectance sensor, whether the sensor 106 is a finger, hand, foot, forehead, or ear sensor, whether the sensor 106 is a stereo sensor or a two-headed sensor, sensor life data indicating whether some or all sensor components have expired and should be replaced, encryption information, keys, indexes to keys or hash functions, and the like, monitor or algorithm upgrade instructions or data, some or all of parameter equations, information about the patient, age, sex, medications, and other information that can be useful for the accuracy or alarm settings and sensitivities, trend history, alarm history, and the like. In an embodiment, the monitor can advantageously store data on the memory device, including, for example, measured trending data for any number of parameters for any number of patients, and the like, sensor use or expiration calculations, sensor history, and the like. Alternatively, memory device 222 can be in the patient monitor 102 on either the processing board 204 or the host instrument 208

With further reference to FIG. 2, processing board 204 can include a sensor interface 210, a digital signal processor (DSP) 212, and an instrument manager 214. The sensor interface 210 receives the signals from the sensor detector(s) 210 and passes the signals to the DSP 212 for processing into representations of physiological parameters. The signals are then passed to the instrument manager 214, which can further process the parameters for display by the host instrument 208. Either or both of the DSP 212 and the instrument manager 214 can include a memory device capable of storing the instructions used to process the data and perform other tasks. In some embodiments, the DSP 212 also communicates with the memory 222. The elements of processing board 204 provide processing of the sensor 106 signals.

In an embodiment, the processing board 204 further includes an environmental conditions module 230 in communication with the instrument manager 214. Although not illustrated in FIG. 2, the environmental conditions module 230 can also, or alternatively, be in direct communication with the DSP 212. The environmental conditions module 230 can provide information relating to the environmental conditions internal or external to the patient monitor. As noted above, it has been discovered that varying environmental conditions, such as atmospheric pressure, altitude, humidity, temperature and the like can affect the output and/or processing of the measurements of physiological parameters. Thus, the patient monitor 102 can use the data provided by the environmental conditions module to account for environmental conditions when processing the signals indicative of one or more physiological parameters. Empirical data regarding the effects of environmental conditions on the processing of the physiological parameters can be obtained to determine the appropriate calibration requirements for the patient monitor 102. For example, the physiological parameter measurement data collected from patients at a low altitude can be compared with similar data collected from patients at a higher altitude to determine the appropriate calibration requirements of the patient monitor 102. In addition, or alternatively, blood samples of patients at both the high altitude and low altitude can be used to compare the non-invasive physiological parameter measurements with the invasive physiological parameter measurements to calibrate the patient monitor 102. Similar data can be collected by comparing patient data collected at different temperatures, humidity, atmospheric pressure, and the like, using either the invasive physiological parameter measurement data, the non-invasive physiological parameter measurement data, or a combination of the two.

In an embodiment, the environmental conditions module 230 can comprise an altimeter, barometer, hygrometer, and/or thermometer, and the like. The altimeter can be a pressure altimeter, GPS altimeter, or similar device capable of approximating the altitude of an object above a predefined level. The barometer can be water-based, mercury based, aneroid based, a barograph, or similar device capable of measuring atmospheric pressure. The hygrometer can be any one of various devices, such as a psychrometer, known in the art that is capable of measuring humidity. The thermometer can be any one of various devices capable of measuring temperature. The environmental conditions module 230 can further comprise additional devices capable of measuring other environmental conditions.

The environmental conditions module 230 can further comprise a processing board or chip, a general purpose processor running appropriate software, or hardware capable of converting the various environmental readings, such as atmospheric pressure, altitude, humidity, and/or temperature, and the like, into a format that is useable by the DSP 212 and/or instrument manager 214.

The environmental conditions module 230 can further be incorporated within the instrument manager 214 or be maintained as a separate component (as illustrated in FIG. 2). The data received from the environmental conditions module 230 can be used by the instrument manager 214 and/or DSP 212 in determining $SpO_2$, Hb, $HbO_2$, SpHb™, SpCO®, SpOC™, SpMet®, PI, PVI®, PR, temperature, and/or other parameters. Thus, the patient monitor 102 can be configured to account for different environmental conditions, such as different altitude, different atmospheric pressure, different humidity, and/or different temperatures, in processing the measured parameters. The patient monitor can then display the physiological parameters in light of the environmental conditions, such as altitude, atmospheric pressure, humidity, and/or temperature. In other words, the patient monitor can correct for various environmental conditions to improve the accuracy of the physiological parameter measurements, or determine the measurements of the physiological parameters based on the environmental conditions.

The patient monitor 102 can account for the environmental conditions and process the various parameters dynamically and/or by using a lookup table. In accounting for the environmental conditions dynamically, the patient monitor 102 can use the data indicative of environmental conditions as it processes the signals indicative of one or more physiological parameters. In another embodiment, the patient monitor 102 can use a look up table residing on the processing board 204, and/or host instrument 208 to account for the altitude and/or atmospheric pressure. The lookup table can include various ranges of environmental conditions and contain a value indicating how the various parameters should be processed in light of the environmental conditions. For example, for each increase in altitude by 10 ft., 100 ft, or 1000 ft., etc., the lookup table can contain a different value to be used to calculate the physiological parameter measurements at the specified altitude. Alternatively, the lookup table can include more than one environmental condition. For example, the lookup table can include ranges for temperature, altitude, atmospheric pressure, humidity and the like. Based on the combination of the measured temperature, altitude, atmospheric pressure, humidity, etc., the lookup table can provide a value to be used to calculate the physiological parameter measurements. The lookup table can in addition include the physiological parameter measurement or the signal received from the sensor as a variable. Thus, based on the measured temperature, altitude, atmospheric pressure, humidity, etc. and physiological parameter measurement or signal received from the sensor, the lookup table can output an adjusted physiological parameter measurement or an adjusted signal. In this manner, the use of the lookup table can decrease the amount of processing required by the patient monitor 102 in accounting for different environmental conditions. Alternatively, the lookup table can be located in the environmental conditions module 230.

In an alternative embodiment, the environmental conditions module 230 can be located on the sensor 106. In such an embodiment, the sensor 106 can include a lookup table similar to that described above and/or can simply send the readings from the environmental conditions module 230 to the patient monitor 102 for processing.

In yet an alternative embodiment, the patient monitor can receive environmental conditions data, such as altitude, atmospheric pressure, humidity, and/or temperature, and the like, from a user or other external system, such as a computer, the Internet or an intranet, mobile device, and the like. In such an embodiment, the processing board 204 may not include an environmental conditions module 230. As discussed above, the processing board 204 can account for the altitude and/or atmospheric pressure data received from an external device or user to determine the readings for various parameters. In an embodiment a user can enter the data indicative of environmental conditions using the control buttons 110, keypad 228, and/or display (108/224), or in some other manner. As mentioned previously, the patient monitor 102 can account for one or more environmental conditions dynamically and/or use a lookup table.

With continued reference to FIG. 2 the patient monitor 102 further includes the host instrument 208. In an embodiment, the host instrument 208 communicates with the board 204 to receive signals indicative of one or more physiological parameters calculated by the DSP 212. The host instrument 208 preferably includes one or more display devices 224 capable of displaying indicia representative of the calculated physiological parameters of the tissue 218 at the measurement site. In an embodiment, the display devices 224 can correspond with the display 108 of FIG. 1. In an embodiment, the host instrument 208 can advantageously comprise a handheld housing capable of displaying one or more of PR, plethysmograph data, perfusion quality such as a perfusion quality index ("PI™"), signal or measurement quality ("SQ"), values and/or trends of blood constituents in body tissue including, for example, $SpO_2$, Hb, $HbO_2$, SpHb™, SpCO®, SpOC™, SpMet®, PI, PVI®, and the like. In other embodiments, the host instrument 208 is capable of displaying values for one or more blood glucose, bilirubin, and the like. The host instrument 208 can be capable of storing or displaying historical or trending data related to one or more of the measured values, combinations of the measured values, plethysmograph data, and the like. The host instrument 208 also includes an audio indicator 226 and user input device 228, such as, for example, a keypad, touch screen, pointing device, voice recognition device, and the like, which can correspond to control buttons 110 of FIG. 1.

In still additional embodiments, the host instrument 208 includes audio or visual alarms that alert caregivers that one or more physiological parameters are falling below predetermined safe thresholds. The host instrument 208 can include indications of the confidence a caregiver should have in the displayed data. In a further embodiment, the host instrument 208 can advantageously include circuitry capable of determining the expiration or overuse of components of the sensor 106, including, for example, reusable elements, disposable elements, or combinations of the same.

Although described in terms of certain embodiments, other embodiments or combination of embodiments will be apparent to those of ordinary skill in the art from the disclosure herein. For example, the monitor 202 can comprise one or more monitoring systems monitoring parameters, such as, for example, vital signs, blood pressure, ECG or EKG, respiration, glucose, bilirubin, and the like. Such systems can combine other information with intensity-derived information to influence diagnosis or device operation. Moreover, the monitor 202 can advantageously include an audio system, preferably comprising a high quality audio processor and high quality speakers to provide for voiced alarms, messaging, and the like. In an embodiment, the monitor 202 can advantageously include an audio out jack, conventional audio jacks, headphone jacks, and the like, such that any of the display information disclosed herein can be audiblized for a listener. For example, the monitor 202 can include an audible transducer input (such as a microphone, piezoelectric sensor, and the like) for collecting one or more of heart sounds, lung sounds, trachea sounds, or other body sounds and such sounds can be reproduced through the audio system and output from the monitor 202. Also, wired or wireless communications (such as Bluetooth or WiFi, including IEEE 801.11a, b, or g), mobile communications, combinations of the same, and the like, can be used to transmit the audio output to other audio transducers separate from the monitor 202.

Figure 3:
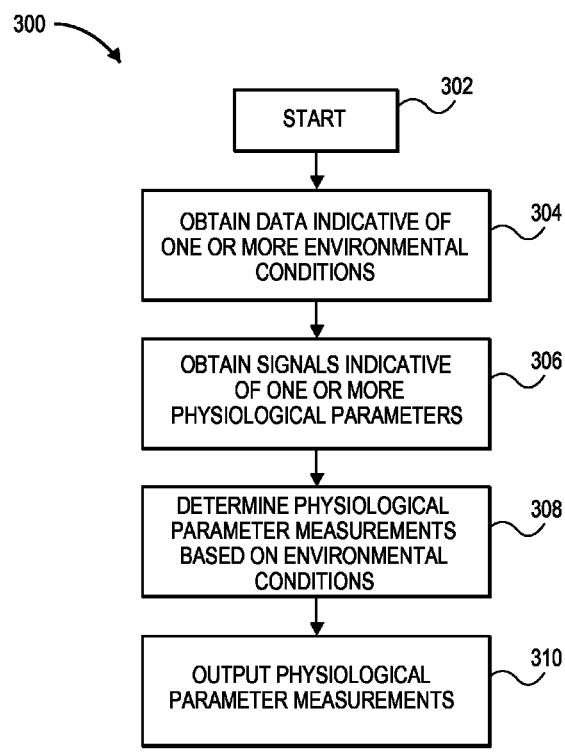
FIG. 3 is a flow diagram illustrative of an embodiment of a routine implemented by a patient monitor for accounting for one or more environmental conditions to process data indicative of one or more physiological parameters.

FIG. 3 is a flow diagram illustrative of one embodiment of a routine 300 implemented by the patient monitor 102 to determine one or more measurement of one or more physiological parameters based on one or more environmental conditions. One skilled in the relevant art will appreciate that the elements outlined for routine 300 can be implemented by one or many computing devices/components that are associated with the patient monitor 102. Accordingly, routine 300 has been logically associated as being generally performed by the patient monitor 102, and thus the following illustrative embodiments should not be construed as limiting.

At block 302, the patient monitor 102 initiates routine 300. At block 304, the patient monitor 102 obtains data indicative of environmental conditions. The environmental conditions can include, but are not limited to, atmospheric pressure, altitude, humidity, temperature, and the like. The data can be obtained from the environmental conditions module 230 internal to the patient monitor, or from an external source as discussed previously. The sensors of the environmental conditions module 230 can be located inside or outside the patient monitor and can include an altimeter, barometer, hygrometer, thermometer, and the like, as described above with reference to FIG. 2. In one embodiment, the environmental conditions module 230 can be located external to the patient monitor, such as, for example, in the sensor 106. Alternatively, the data indicative of environmental conditions can be obtained from another computer, the Internet or an intranet, a user, mobile device, and the like. In an embodiment where the environmental conditions data is obtained from a user, the user can enter the data using the control buttons 110, keypad 228, and/or display (108/224).

At block 306, the patient monitor 102 obtains signals indicative of one or more physiological parameters. The physiological parameters can include, but are not limited to SpO$_2$, SpHb™, SpCO®, SpOC™, SpMet®, PI, PVI®, PR, and the like. Typically, these signals are received from a sensor 106, as described above with reference to FIG. 2.

At block 308, the patient monitor 102 determines physiological parameter measurements based on the signals indicative of one or more physiological parameters and the environmental conditions. The effects of the environmental conditions on the physiological parameter measurements can be determined based on empirically collected data from patients to form a calibration curve. The data from the patients can be collected in different environmental conditions using invasive and/or non-invasive measurement techniques, as described in greater detail above. Using the calibration curve, the patient monitor can be configured to adjust the signals obtained from the sensor 106 to calculate an adjusted physiological parameter measurement based on the adjusted signal. Alternatively, the patient monitor can adjust the physiological parameter measurement based on the environmental conditions after the physiological parameter measurement has been calculated using the raw, or unadjusted, signals received from the sensor. A lookup table can be used in either case to adjust the signals or the physiological parameter measurement based on the environmental conditions, as described in greater detail above.

Furthermore, the patient monitor 102 can determine the physiological parameter measurements based on the environmental conditions in a variety of ways. In one embodiment, the patient monitor 102 is pre-configured, or pre-calibrated based on the environmental conditions. For example, a patient monitor located at an elevation of 5000 ft. can be calibrated differently than a patient monitor at sea level using the calibration curve. Patient monitors located in areas with different humidity, temperature, and/or atmospheric pressure can be similarly pre-calibrated. The calibrations can be encoded into the patient monitor so that all physiological parameter measurements are adjusted in a similar manner. The patient monitors can be calibrated during manufacturing, assembly, or at the patient site. In an alternative embodiment, the patient monitor determines the appropriate adjustments for the physiological parameter measurements based on recently determined environmental conditions. In this embodiment, a lookup table can be used to determine the appropriate adjustments based on the environmental conditions, as discussed in greater detail above. In an embodiment, the monitor can also be configured to adjust measurements during the course of monitoring. This can be advantageous, for example, during a life flight or other travel via air or over land where altitude and humidity changes occur during the course of monitoring.

Once the physiological parameter measurement has been determined based on environmental conditions, the patient monitor 102 outputs the physiological parameter measurement, as illustrated in block 310. The patient monitor 102 can output the physiological parameter measurement to the display 224, to another patient monitor, a computer, a database, a mobile device, or the like. The display 224 can display both the measurement based on environmental conditions as well as a measurement not accounting for the environmental conditions. In this way, a user can verify any differences between the two measurements.

With further reference to FIG. 3 it is to be understood that fewer or more blocks can be used and that the order of the blocks can be changed without affecting the nature or scope of the description. For example, the process 300 can obtain data indicative of one or more environmental conditions and obtain signals indicative of one or more physiological parameters simultaneously. In addition, the process 300 can include a block for referring to a lookup table to determine the adjustment for the physiological parameter measurement.

It will be appreciated by those skilled in the art and others that all of the functions described in this disclosure can be embodied in software executed by one or more processors of the disclosed components and mobile communication devices. The software can be persistently stored in any type of non-volatile storage.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without party input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art. It will further be appreciated that the data and/or components described above may be stored on a computer-readable medium and loaded into memory of the computing device using a drive mechanism associated with a computer readable storing the computer executable components such as a CD-ROM, DVD-ROM, or network interface further, the component and/or data can be included in a single device or distributed in any manner. Accordingly, general purpose computing devices may be configured to implement the processes, algorithms and methodology of the present disclosure with the processing and/or execution of the various data and/or components described above.

It should be emphasized that many variations and modifications may be made to the above-described embodiments, the elements of which are to be understood as being among other acceptable examples. All such modifications and variations are intended to be included herein within the scope of this disclosure and protected by the following claims.

The invention claimed is:

1. A patient monitoring system configured to determine one or more measurements of one or more physiological parameters, the patient monitoring system comprising:
    an environmental conditions module configured to determine one or more environmental conditions comprising at least one of atmospheric pressure, altitude, humidity, and temperature;
    a physiological sensor configured to sense light after it has passed through tissue of a patient and generate a signal indicative of one or more physiological parameters in response to the sensed light; and
    a patient monitor in communication with the physiological sensor and the environmental conditions module, wherein the patient monitor is configured to:
        receive the signal,
        determine one or more measurements of the one or more physiological parameters from the received signal, and
        adjust the one or more measurements of the one or more physiological parameters based at least on the determined one or more environmental conditions.

2. The patient monitoring system of claim 1, wherein the one or more physiological parameters comprise at least one of oxygen saturation ($SpO_2$), hemoglobin (Hb), oxyhemoglobin ($HbO_2$), total hemoglobin (SpHb™), carboxyhemoglobin (SpCO®), methemoglobin (SpMet®), total oxygen content (SpOC™), perfusion index (PI), pleth variability index (PVI®), pulse rate (PR), and temperature.

3. The patient monitoring system of claim 1, wherein the environmental conditions module is located external to the patient monitor.

4. The patient monitoring system of claim 1, wherein the patient monitor is further configured to adjust the one or more measurements of the one or more physiological parameters based at least on data collected from patients in different environmental conditions.

5. A patient monitoring system configured to determine one or more measurements of one or more physiological parameters, the patient monitoring system comprising:
    an environmental conditions module configured to determine one or more environmental conditions, and comprising at least one of a barometer, an altimeter, a hygrometer, and a thermometer;
    a physiological sensor configured to sense light after it has passed through tissue of a patient and generate a signal indicative of one or more physiological parameters in response to the sensed light; and
    a patient monitor in communication with the physiological sensor and the environmental conditions module, wherein the patient monitor is configured to:
        receive the signal,
        determine one or more measurements of the one or more physiological parameters from the received signal, and
        adjust the one or more measurements of the one or more physiological parameters based at least on the determined one or more environmental conditions.

6. A patient monitoring system configured to determine one or more measurements of one or more physiological parameters, the patient monitoring system comprising:
    a physiological sensor configured to sense light after it has passed through tissue of a patient and generate a signal indicative of one or more physiological parameters based at least on the sensed light;
    a patient monitor in communication with the physiological sensor; and
    an environmental conditions module located within the patient monitor and configured to determine one or more environmental conditions,
    wherein the patient monitor is configured to:
        receive the signal,
        determine one or more measurements of the one or more physiological parameters from the received signal, and
        adjust the one or more measurements of the one or more physiological parameters based at least on the determined one or more environmental conditions.

7. A patient monitoring system configured to determine one or more measurements of one or more physiological parameters, the patient monitoring system comprising:
    a physiological sensor configured to sense light after it has passed through tissue of a patient and generate a signal indicative of one or more physiological parameters based at least on the sensed light;
    a patient monitor in communication with the physiological sensor; and
    an environmental conditions module in communication with the patient monitor and configured to obtain data indicative of one or more environmental conditions from at least one of a separate patient monitor, a separate computer, a user, an intranet and Internet,
    wherein the patient monitor is configured to:
        receive the signal, determine one or more measurements of the one or more physiological parameters from the received signal, and adjust the one or more measurements of the one or more physiological parameters based at least on the data indicative of one or more environmental conditions.

8. A patient monitoring system configured to determine one or more measurements of one or more physiological parameters, the patient monitoring system comprising:
a physiological sensor configured to sense light after it has passed through tissue of a patient and generate a signal indicative of one or more physiological parameters based at least on the sensed light;
an environmental conditions module configured to determine one or more environmental conditions; and
a patient monitor in communication with the physiological sensor and the environmental conditions module, wherein the patient monitor is configured to:
receive the signal,
determine one or more measurements of the one or more physiological parameters from the received signal, and
adjust the one or more measurements of the one or more physiological parameters based at least on the determined one or more environmental conditions,
wherein the patient monitor includes a lookup table comprising a plurality of values used to determine the one or more measurements of the one or more physiological parameters based at least on the one or more environmental conditions.

9. The patient monitoring system of claim 8, wherein values in the lookup table are calculated based on empirically collected data from patients.

10. A patient monitor configured to determine one or more measurements of one or more physiological parameters, the patient monitor comprising:
an environmental conditions module configured to obtain data indicative of one or more environmental conditions comprising at least one of atmospheric pressure, altitude, humidity, and temperature; and
a processing board in communication with a physiological sensor and the environmental conditions module, wherein the patient monitor is configured to:
obtain at least one signal indicative of one or more physiological parameters from the physiological sensor, wherein the physiological sensor generates the at least one signal in response to light detected after it has passed through tissue of a patient,
determine one or more measurements of one or more physiological parameters from the at least one signal, and
adjust the one or more measurements of the one or more physiological parameters based at least on the data indicative of one or more environmental conditions.

11. The patient monitor of claim 10, wherein the one or more physiological parameters comprise at least one of oxygen saturation (SpO$_2$), hemoglobin (Hb), oxyhemoglobin (HbO$_2$), total hemoglobin (SpHb™), carboxyhemoglobin (SpCO®), methemoglobin (SpMet®), total oxygen content (SpOC™), perfusion index (PI), pleth variability index (PVI®), pulse rate (PR), and temperature.

12. The patient monitor of claim 10, wherein the processing board is further configured to adjust the one or more measurements of the one or more physiological parameters based at least on data collected from patients in different environmental conditions.

13. A patient monitor configured to determine one or more measurements of one or more physiological parameters, the patient monitor comprising:
an environmental conditions module configured to obtain data indicative of one or more environmental conditions, and comprising at least one of a barometer, an altimeter, a hygrometer, and a thermometer; and
a processing board in communication with the environmental conditions module and a physiological sensor, wherein the processing board is configured to:
obtain at least one signal indicative of one or more physiological parameters from the physiological sensor, wherein the physiological sensor generates the at least one signal in response to light detected after it has passed through tissue of a patient,
determine one or more measurements of one or more physiological parameters from the at least one signal, and
adjust the one or more measurements of the one or more physiological parameters in response to the one or more environmental conditions.

14. A patient monitor configured to determine one or more measurements of one or more physiological parameters, the patient monitor comprising:
a processing board in communication with a physiological sensor; and
an environmental conditions module in communication with the patient monitor and configured to obtain data indicative of one or more environmental conditions from at least one of a separate processing board, a separate computer, a user, an intranet and Internet
wherein the processing board is configured to:
obtain at least one signal indicative of one or more physiological parameters from the physiological sensor, wherein the physiological sensor generates the at least one signal based at least on light detected after it has passed through tissue of a patient,
determine one or more measurements of one or more physiological parameters from the at least one signal, and
adjust the one or more measurements of the one or more physiological parameters based at least on the data indicative of one or more environmental conditions.

15. A patient monitor configured to determine one or more measurements of one or more physiological parameters, the patient monitor comprising:
an environmental conditions module configured to obtain data indicative of one or more environmental conditions; and
a processing board in communication with the environmental conditions module and a physiological sensor, wherein the processing board is configured to:
obtain at least one signal indicative of one or more physiological parameters from the physiological sensor, wherein the physiological sensor generates the at least one signal based at least on light detected after it has passed through tissue of a patient,
determine one or more measurements of one or more physiological parameters from the at least one signal, and
adjust the one or more measurements of the one or more physiological parameters based at least on the data indicative of one or more environmental conditions, wherein the patient monitor includes a lookup table comprising a plurality of values used to determine the one or more measurements of the one or more physiological parameters based at least on the one or more environmental conditions.

16. The patient monitor of claim 15, wherein values in the lookup table are calculated based on empirically collected data from patients.

17. A computer-implemented method for determining one or more measurements of one or more physiological parameters, the computer-implemented method comprising:

under control of one or more computing devices:
obtaining data indicative of one or more environmental conditions comprising at least one of atmospheric pressure, altitude, humidity, and temperature;
obtaining a signal indicative of one or more physiological parameters from a physiological sensor, wherein the physiological sensor generates the signal in response to light detected after it has passed through tissue of a patient;
determining one or more measurements of the one or more physiological parameters from the signal; and
adjusting the one or more measurements of the one or more physiological parameters based at least on the one or more environmental conditions.

18. The computer-implemented method of claim 17, wherein the one or more physiological parameters comprises at least one of oxygen saturation ($SpO_2$), hemoglobin (Hb), oxyhemoglobin ($HbO_2$), total hemoglobin (SpHb™), carboxyhemoglobin (SpCO®), methemoglobin (SpMet®), total oxygen content (SpOC™), perfusion index (PI), pleth variability index (PVI®), pulse rate (PR), and temperature.

19. The computer-implemented method of claim 17, wherein adjusting the one or more measurements of the one or more physiological parameters is further based at least on data collected from patients in different environmental conditions.

20. A computer-implemented method for determining one or more measurements of one or more physiological parameters, the computer-implemented method comprising:

obtaining data indicative of one or more environmental conditions from at least one of a barometer, an altimeter, a hygrometer, and a thermometer;
obtaining a signal indicative of one or more physiological parameters from a physiological sensor, wherein the physiological sensor generates the signal in response to light detected after it has passed through tissue of a patient;
determining one or more measurements of the one or more physiological parameters from the signal; and
adjusting the one or more measurements of the one or more physiological parameters based at least on the one or more environmental conditions.

* * * * *